United States Patent [19]

Suzuki et al.

[11] 4,079,180
[45] Mar. 14, 1978

[54] PROCESS FOR PREPARING 7-AMINOCEPHALOSPORANIC ACID DERIVATIVES

[75] Inventors: Nobuyuki Suzuki, Hyuga; Tsuneo Sowa; Masahiro Murakami, both of Nobeoka, all of Japan

[73] Assignee: Asahi Kasei Kogyo Kabushiki Kaisha, Osaka, Japan

[21] Appl. No.: 650,701

[22] Filed: Jan. 20, 1976

[30] Foreign Application Priority Data

Jan. 22, 1975 Japan .................................. 50-8636
Jul. 9, 1975 Japan .................................. 50-83574
Jul. 9, 1975 Japan .................................. 50-83575

[51] Int. Cl.² .......................................... C07D 501/04
[52] U.S. Cl. .......................................... 544/24; 544/30
[58] Field of Search ............... 260/243 C; 544/24, 30

[56] References Cited

U.S. PATENT DOCUMENTS

| 3,928,324 | 12/1975 | Rosati ............... | 260/243 C |
| 3,932,392 | 1/1976 | Johnson et al. ....... | 260/243 C |
| 3,962,223 | 6/1976 | Martel et al. ........ | 260/243 C |

*Primary Examiner*—Donald G. Daus
*Assistant Examiner*—Diana G. Rivers
*Attorney, Agent, or Firm*—Armstrong, Nikaido, Marmelstein & Kubovcik

[57] ABSTRACT

7-Aminocephalosporanic acid derivatives represented by the general formula (III),

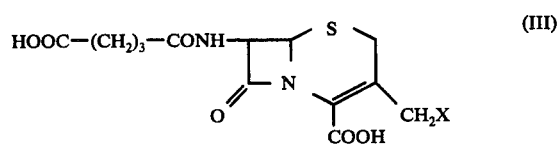

wherein X is hydrogen, hydroxyl, acetate or a nucleophilic residue, which are useful as a starting material for the synthesis of cephalosporin type antibiotics low in toxicity and broad in pharmacological effect can be easily prepared by allowing to react cephalosporin C or its derivative represented by the general formula (I),

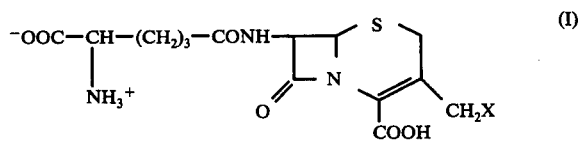

wherein X is as defined above, or a salt thereof with an α-keto derivative represented by the general formula (II),

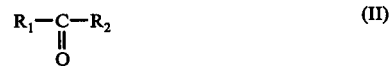

wherein $R_1$ is carboxyl, aroyl or amide when $R_2$ is hydrogen, and is carboxyl when $R_2$ is alkyl or aryl, or its salt. In this case, the yield of the 7-aminocephalosporanic acid derivatives can be remarkably improved by carrying out the reaction in the presence of hydrogen peroxide. The yield can be further improved by adding thiosulfuric acid or a salt thereof after the completion of the reaction to decompose the unreacted hydrogen peroxide.

20 Claims, No Drawings

PROCESS FOR PREPARING 7-AMINOCEPHALOSPORANIC ACID DERIVATIVES

This invention relates to a process for preparing 7-aminocephalosporanic acid derivatives.

More particularly, the invention pertains to a process in which cephalosporin C or its derivative represented by the general formula (I),

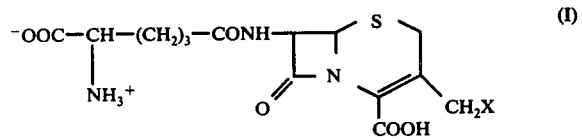

wherein X is hydrogen, hydroxyl, acetate or a nucleophilic residue, or a salt thereof (hereinafter abbreviated to "the cephalosporin compound") is allowed to react in the absence or presence of hydrogen peroxide with an α-keto derivative represented by the general formula (II),

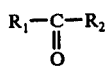

wherein $R_1$ is carboxyl, aroyl or amide when $R_2$ is hydrogen, and is a carboxyl group when $R_2$ is alkyl or aryl, or its salt (hereinafter abbreviated to "the α-keto derivative") to obtain a 7-aminocephalosporanic acid derivative represented by the general formula (III),

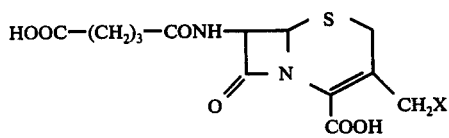

wherein X is as defined above.

An object of the present invention is to provide a commercial scale process for producing, at low cost and with ease, 7-aminocephalosporanic acid derivatives which are starting materials for the synthesis of cephalosporin type antibiotics low in toxicity and broad in pharmacological effect.

As processes for preparing the 7-aminocephalosporanic acid derivative (III), there have heretofore been known such processes that the cephalosporin compound (I) obtained by fermentation is converted into the 7-aminocephalosporanic acid derivative (III) by use of D-amino acid oxidase (Belgian Pat. No. 736934, Japanese Patent Kokai (Laid-Open) No. 39595/72 and Japanese Patent Publication No. 7158/75). According to these processes, a large amount of an α-ketoadipoyl 7-aminocephalosporanic acid or its derivative (hereinafter referred to as "α-ketoadipoyl 7-ACA derivative") represented by the formula (IV),

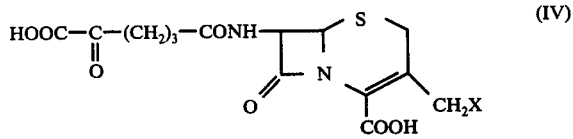

wherein X is as defined above, is formed as an intermediate. In order to inhibit the formation of said α-ketoadipoyl 7-ACA derivative (IV), there has been reported such procedure that sodium azide or the like enzyme inhibitor is made present in the reaction system.

However, the above-mentioned processes have such disadvantages that enormous equipments are required for the commercial scale production of D-amino acid oxidase, that sodium axide or the like enzyme inhibitor, which is injurious to the human body, is required to be used in large quantities, and that the stable production of the end product is effected with difficulty, and hence are not always said to be advantageous as commercial scale processes.

In view of the above-mentioned disadvantages of the prior art processes, the present inventors repeated extensive studies on an entirely novel process not belonging to any of the above-mentioned categories to find that 7-aminocephalosporanic acid derivatives can be obtained in high yields by treating the cephalosporin compound with the α-keto derivative, if desired in the presence of hydrogen peroxide. Based on the above finding, the inventors have accomplished the present invention.

According to the present invention, there is provided a process for preparing the α-ketoadipoyl 7-ACA derivative represented by the formula (IV),

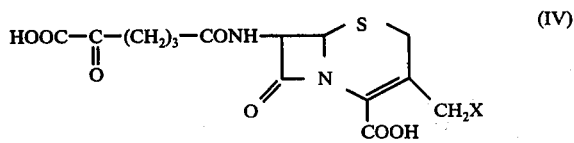

wherein X is hydrogen, hydroxyl, acetate or a nucleophilic residue, and 7-aminocephalosporanic acid derivatives represented by the formula (III),

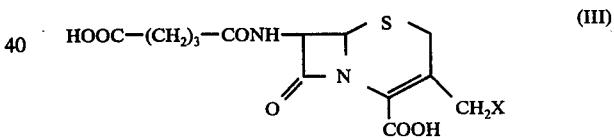

wherein X is as defined above, which comprises allowing to react cephalosporin C or its derivative represented by the formula (I),

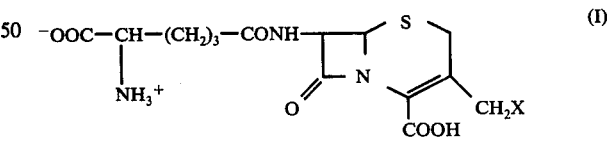

wherein X is as defined above, or a salt thereof with an α-keto derivative represented by the formula (II),

wherein $R_1$ is carboxyl, aroyl or amide when $R_2$ is hydrogen, and is carboxyl when $R_2$ is alkyl or aryl, or its salt. There is further provided a process for preparing 7-aminocephalosporanic acid derivatives of the formula (III), which comprises allowing to react cephalosporin C or its derivative represented by the formula (I) or a salt thereof with an α-keto derivative of the formula (II) or its salt in the presence of hydrogen peroxide.

Thus, the reaction of obtaining the α-ketoadipoyl 7-ACA derivative from the cephalosporin compound is carried out by reacting the cephalosporin compound in an aqueous solution with the α-keto derivative, while the reaction of preparing the 7-aminocephalosporanic acid derivative from the α-keto derivative is chiefly carried out by reacting the α-ketoadipoyl 7-ACA derivative in an aqueous solution, if desired with hydrogen peroxide.

Although a 7-aminocephalosporanic acid derivative is formed in the reaction of forming the α-ketoadipoyl 7-ACA derivative by reacting the cephalosporin compound with the α-keto derivative, the α-ketoadipoyl 7-ACA derivative formed as an intermediate is extremely chemically unstable. According to an embodiment of the present invention the formed intermediate α-ketoadipoyl 7-ACA derivative is led to a stable 7-aminocephalosporanic acid derivative by making hydrogen peroxide present in the reaction system, if desired, thereby obtaining the 7-aminocephalosporanic acid derivative selectively and in high yield.

(i) The reaction of obtaining the α-ketoadipoyl 7-ACA derivative from the cephalosporin compound is carried out by reacting the cephalosporin compound in an aqueous solution with the α-keto derivative.

Preferable as the α-keto derivative used in the present process are glyoxylic acid, pyruvic acid, phenylglyoxal, glyoxylic acid amide, α-ketophenylacetic acid, sodium α-keto-n-butanoate, α-keto-n-butanoic acid and sodium glyoxylate. Among these, glyoxylic acid is most preferable from the standpoint of the yield of 7-aminocephalosporanic acid. The reaction proceeds most efficiently at a pH in the range from 3.0 to 8.0, particularly from 3.5 to 6.0. If the pH at the time of reaction exceeds 8.0, the cephalosporin compound and the α-ketoadipoyl 7ACA derivative become unstable and are decomposed to cause side reactions, with the result that the yield of the desired α-ketoadipoyl 7-ACA derivative or 7-aminocephalosporanic acid derivative is undesirably lowered. The amount of the α-keto derivative used in the present invention may stoichiometrically be at least equimolar to the starting cephalosporin compound, but is properly increased according to other conditions, e.g. the kind of cephalosporin compound, the reaction temperature, and the kind and amount of co-existing impurities, and is preferably from 1 to 50 times the mole of the cephalosporin compound. The use of an unnecessarily large amount of α-keto derivative is not economical, though no particular influence is produced on the reaction.

In the present process, it is particularly effective to accelerate the rate of reaction of the cephalosporin compound with the α-keto derivative by addition of a salt comprising a metal such as copper, manganese, calcium, aluminum, iron, nickel, cobalt, or zinc, and an acid such as sulfuric, acetic, propionic or hydrochloric acid. The metal salt is preferably used in an amount in the range from 1/10 to 20 times the mole of the cephalosporin compound. If desired, an organic base may be used in combination with or in place of the said metal salt to shorten the reaction time. In this case, the formation of side reaction products can be inhibited to give more favorable results. Preferable as the organic base is a tertiary cyclic amine such as pyridine, a secondary cyclic amine such as imidazole, or a chain amine such as triethylamine, dimethylamine or methylamine. The amount of the organic base to be added is properly decided according to the kind thereof and other reaction conditions, but is preferably from 1 to 30 times the mole of the cephalosporin compound. The use of an unnecessarily large amount of the organic base makes the purification of the desired 7-aminocephalosporanic acid derivative difficult, and hence is not always desirable.

In the present process, the reaction is effected at a temperature in the range from 0° to 50° C. However, the cephalosporin compound used as starting material and the α-ketoadipoyl 7-ACA derivative obtained as intermediate are chemically unstable, so that it is not preferable to carry out the reaction at an unnecessarily high temperature. Most economically, the reaction is effected at below the so-called room temperature. Further, the reaction time in the present process is properly decided according to other reaction conditions, e.g. the presence or absence of the metal salt or organic base, the hydrogen ion concentration at the time of reaction, and the reaction temperature. In case the metal salt or organic base is not present, the reaction time in the present process is 3 to 24 hours, while in the presence of the metal salt or organic base, the reaction terminates within such a short period of time as 5 minutes to 4 hours.

| Metal salt | Organic base | Reaction time (hours) | Yield* (%) |
|---|---|---|---|
| No | No | 5.0 | 56.4 |
| No | Yes | 2.0 | 77.1 |
| Yes | No | 2.0 | 77.3 |
| Yes | Yes | 1.0 | 92.0 |

*Yield of 7-aminocephalosporanic acid derivative (ii) As mentioned previously, the α-ketoadipoyl 7-ACA derivative is extremely chemically unstable, and is converted into a 7-aminocophalosporanic acid derivative by acid treatment or by extension of reaction time. However, the α-ketoadipoyl 7-ACA derivative does not completely disappear from the reaction liquid, and the separation thereof is quite difficult. Accordingly, in case a 7-aminocephalosporanic acid derivative is desired to be obtained, the α-ketoadipoyl 7-ACA derivative present in the reaction liquid is reacted with hydrogen peroxide.

For incorporation of hydrogen peroxide into the reaction system, there may be adopted any of such procedure that hydrogen peroxide or its aqueous solution is added to the reaction system, or a compound capable of forming hydrogen peroxide within the reaction system, e.g. sodium perborate, is added to the reaction system.

The amount of the hydrogen peroxide used in the present invention somewhat varies depending on other conditions, e.g. pH of the reaction mixture, the reaction temperature, and the kind and concentration of the cephalosporin compound used as starting material, but is preferably from 1 to 30 times the mole of the cephalosporin compound. The starting cephalosporin compound and the end product 7-aminocephalosporanic acid derivative are easily oxidized to cause decomposition of the cephem rings thereof. Accordingly, the use of an unnecessarily large amount of hydrogen peroxide is not desirable. The reaction of obtaining the 7-aminocephalosporanic acid derivative by reaction of the α-ketoadipoyl 7-ACA derivative with hydrogen peroxide preceeds most efficiently at an acidic pH in the range from 2.0 to 6.0, preferably from 3.0 to 5.5. It is quite advantageous that the optimum pH in the reaction of obtaining the 7-aminocephalosporanic acid derivative from the α-ketoadipoyl 7-ACA derivative is substantially identical with the optimum pH in the reaction of obtaining the α-ketoadipoyl 7-ACA derivative from the cephalosporin compound. It is also advantageous that the metal salt or organic base, which, if desired, is used in the reaction of obtaining the 7-aminocephalosporanic acid derivative from the cephalosporin compound, has no detrimental effect on the reaction of obtaining the 7-aminocephalosporanic acid derivative by treating the α-ketoadipoyl 7-ACA derivative with hydrogen peroxide. At an alkaline pH, the rate of reaction of the α-ketoadipoyl 7-ACA derivative with hydrogen peroxide lowers, and the hydrogen peroxide becomes difficultly soluble in the reaction system and thereby is liberated. On the other hand, at an acidic pH exceeding 2.0, the α-ketoadipoyl 7-ACA is unstable, with the result that the yield of the desired 7-aminocephalosporanic acid derivative is undesirably lowered to a great extent.

Hydrogen peroxide used in the present process may be added according to such procedure that it is added after formation of the α-ketoadipoyl 7-ACA derivative from the cephalosporin compound, or such procedure that it is made present from the beginning of reaction of the cephalosporin compound with the α-keto derivative, and the resulting α-ketoadipoyl 7-ACA derivative is led to the 7-aminocephalosporanic acid derivative. Since the α-ketoadipoyl 7-ACA derivative obtained as intermediate is chemically unstable, it is not always desirable to react hydrogen peroxide with the said derivative after purification.

The reaction is terminated by lowering the pH of the reaction liquid to less than 2.0. In case hydrogen peroxide has been used, residual hydrogen peroxide reacts with the 7-aminocephalosporanic acid derivative in the reaction liquid to bring about side reactions. If desired, therefore, it is preferable that the residual hydrogen peroxide is previously removed by reduction. However, the addition of an ordinary chemical called a reducing agent accompanies reduction reactions with the starting cephalosporin compound and the end product 7-aminocephalosporanic acid derivative to cause a chemical change in the cephem nuclei thereof. Accordingly, the use of thiosulfuric acid or its salt is required.

Thus, according to the most preferable embodiment of the present invention, the cephalosporin compound (I) is treated with an α-keto derivative in the presence of hydrogen peroxide, and then isolated in the presence of thiosulfuric acid or its salt, whereby the desired 7-aminocephalosporanic acid derivative (III) can be obtained selectively and in an extremely high yield.

The most preferable embodiment is a process in which an aqueous solution containing the cephalosporin compound is reacted with an α-keto derivative in the presence of hydrogen peroxide, and then reacted with thiosulfuric acid or its salt to obtain the 7-aminocephalosporanic acid derivative. According to this embodiment, the 7-aminocephalosporanic acid derivative can be obtained selectively by dissolving hydrogen peroxide in an aqueous solution containing the cephalosporin compound, adding an α-keto derivative to the solution, reacting the resulting mixture for a definite period of time, and then adding thiosulfuric acid or its salt to the reaction liquid.

A characteristic of this embodiment resides in that the cephalosporin compound is reacted with an α-keto derivative in the presence of hydrogen peroxide, and then reacted with thiosulfuric acid or its salt, thereby selectively obtaining the 7-aminocephalosporanic acid derivative without formation of any side reaction product.

In this embodiment, the amount of thiosulfuric acid or its salt to be added to the reaction system somewhat varies depending on other conditions, e.g. the amount of hydrogen peroxide added to the reaction liquid, the hydrogen ion concentration, the reaction temperature, and the kind and concentration of the cephalosporin compound used as starting material, but is usually at most equimolar to the amount of the $H_2O_2$ used.

The 7-aminocephalosporanic acid derivative obtained according to the process of the present invention can be purified by an ordinary procedure, e.g. by extraction from the reaction solvent by use of an organic solvent such as ethyl acetate, butyl acetate or n-butanol.

Another characteristic of the present process lies in that the reaction can be effected as a reaction in an aqueous solution. Accordingly, the 7-aminocephalosporanic acid derivative can be obtained directly from, for example, a culture liquor of the cephalosporin compound, without isolating and purifying the cephalosporin compound. This is an extremely advantageous point in practicing the present process on commerical scale.

The 7-aminocephalosporanic acid derivatives obtained according to the process of the present invention can be led, by application of the iminoether method, for example, to 3-substituted methyl-7β-aminocephalosporanic acids, for example, which are used as starting material for medicines.

The present invention is illustrated in further detail below with reference to examples, but the examples are illustrative and do not limit the scope of the present process.

EXAMPLE 1

3 Grams of crystals of sodium salt of cephalosporin C having a purity of 74.2% (i.e. 2.2 g. in terms of sodium salt of cephalosporin C) were dissolved in 100 ml. of water. The resulting solution was added with stirring to 200 ml. of an aqueous solution containing 4.7 g. of glyoxylic acid, 0.3 g. of copper acetate and 41 ml. of pyridine. This mixture was stirred at room temperature for 1 hour, and the pH of the mixture was lowered to 2.0 by addition of hydrochloric acid with ice cooling to terminate the reaction. The reaction liquid was extracted 5 times with about 200 ml. of cold ethyl acetate, and the extracts were collected. The collected ethyl acetate extract was concentrated under reduced pressure at below 40° C. to a volume of about 200 ml. and then dried overnight at 5° C. by use of anhydrous sodium sulfate. This liquid was filtered, and the residue was washed with a small amount of ethyl acetate. The filtrate was combined with the washings, and the resulting liquid was quickly concentrated under reduced pressure at below 40° C. to a volume of 20 ml. and then dropped into 120 ml. of petroleum ether with vigorous stirring. This liquid was subjected to centrifugation with cooling, and the supernatant was removed by decantation. Thereafter, the precipitate was suspended in petroleum ether, and the resulting suspension was again subjected to centrifugation with cooling. After removing the supernatant by decantation, the precipitate was quickly dried over alumina in vacuum to obtain 2.5 g. of pale yellow crystals of 3-acetoxymethyl-7β-(5-carboxy-5-oxo-pentanamido)-3-cephem-4-carboxylic acid. (Purity 52%).

TLC Rf = 0.30 PPC Rf = 0.52

EXAMPLE 2

4 Grams of crystals of sodium salt of cephalosporin C having a purity of 74.2% and 3.3 g. of copper acetate were dissolved in 120 ml. of water. At this stage, the pH of the reaction liquid was 3.9. Into this reaction mixture, 120 ml. of an aqueous solution containing 6.24 g. of glyoxylic acid and 5.5 ml. of pyridine was dropped over a period of 1 hour with stirring at room temperature. The pH of the reaction liquid at the time of completion of the reaction was 4.6. Thereafter, the reaction liquid was adjusted to pH 3.0 by addition of 1N sulfuric acid, and 60 cc. of a 15% aqueous hydrogen peroxide solution was dropped into the liquid over a period of 1 hour. The reaction liquid was further stirred for 10 minutes, and then adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 92%. No 3-acetoxymethyl-7β-(5-carboxy-5-oxopentanamido)-3-cephem-4-carboxylic acid was detected.

This reaction liquid was extracted 3 times with 500 ml. of ethyl acetate, and the extracts were collected. The collected ethyl acetate extract was concentrated under reduced pressure at below 40° C. to a volume of about 200 ml. and then dried overnight by use of anhydrous sodium sulfate. This liquid was filtered, and the residue was washed with a small amount of ethyl acetate. The filtrate was combined with the washings, and the resulting liquid was concentrated under reduced pressure at below 40° C. to a volume of 10 ml. and then dropped into 200 ml. of petroleum ether with vigorous stirring. This liquid was subjected to centrifugation, and the supernatant was removed by decantation. Thereafter, the precipitate was suspended in petroleum ether, and the resulting suspension was again subjected to centrifugation. After removing the supernatant by decantation, the precipitate was quickly dried over alumina in vacuum to obtain 2.38 g. of pale yellow crystals of 3-acetoxymethyl-7β-(4-carboxybutanamido)-3-cephem-4-carboxylic acid. Purity 96.9%.

EXAMPLE 3

1.5 Grams of crystals of sodium salt of cephalosporin C having a purity of 74.2% and 406 mg. of copper sulfate were dissolved in 100 ml. of water. The pH of the reaction liquid was 3.9. To this liquid, each 20 ml. of 100 ml. of an aqueous solution containing 2.3 g. of glyoxylic acid and 1.5 ml. of triethylamine was added every 30 minutes. When 10 minutes had elapsed after each addition, each 3 ml. of a 20% aqueous hydrogen peroxide solution was added, and the liquid was reacted with stirring for 30 minutes. The pH of the reaction liquid at the time of completion of the reaction was 3.5. After stirring for additional 30 minutes, the reaction liquid was adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 87.8%.

This reaction liquid was treated in the same manner as in Example 2 to obtain 0.86 g. of pale yellow crystals of 3-acetoxymethyl-7β-(4-carboxybutanamido)-3-cephem-4-carboxylic acid. Purity 95.1%.

EXAMPLE 4

A fermentation liquor of *Cephalosporium acremonium* was freed from the cells by filtration, subjected to acid treatment (pH 2.8) to decompose penicillin N contained therein and then once filtered, and the residue was washed. The filtrate was combined with the washings to obtain 4.6 liters of a liquid containing 3223 γ/ml of cephalosporin C. This liquid was passed through and adsorbed on an active carbon column, washed with water and then eluted with 7 liters of 3% n-butanol containing 700 ml. of 0.3N sodium hydroxide to recover a desired fraction. This fraction was adjusted to pH 6.0 and then concentrated under reduced pressure at below 40° C. to obtain 275 ml. of a pale yellow solution containing 40 mg/ml of cephalosporin C. 100 Milliliters of this solution was adjusted to pH 6.5 by addition of sodium hydroxide and then incorporated with 2.1 g. of zinc acetate. Into the resulting liquid, 500 ml. of an aqueous solution containing 4.6 g. of glyoxylic acid and 9.6 ml. of γ-picoline was dropped over a period of 1.5 hours with stirring at room temperature. During the reaction, sodium hydroxide was added so that the pH of the reaction liquid became 5.0. In this case, a part of the reaction liquid was recovered and subjected to paper chromatography to find that the crude yields of 3-acetoxymethyl-7β-(5-carboxy-5-oxopentanamido)-3-cephem-4-carboxylic acid and 3-acetoxymethyl-7β-(4-carboxybutanamido)-3-cephem-4-carboxylic acid were 61% and 18%, respectively.

The reaction liquid was further stirred for 30 minutes and then lowered in pH to 3.0 by addition of sulfuric acid. Thereafter, 60 ml. of a 35% aqueous hydrogen peroxide solution was dropped into the liquid. After stirring for additional 15 minutes, the liquid was adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 76.1%. No 3-acetoxymethyl-7β-(5-carboxy-5-oxopentanamido)-3-cephem-4-carboxylic acid was detected.

This reaction liquid was treated in the same manner as in Example 2 to obtain 3.38 g. of pale yellow crystals of 3-acetoxymethyl-7β-(4-carboxybutanamido)-3-cephem-4-carboxylic acid. Purity 78.8%.

EXAMPLE 5

A fermentation liquor of *Cephalosporium acremonium* was freed from the cells by filtration, subjected to acid treatment (pH 2.8) to decompose pencillin N contained therein and then again filtered, and the residue was washed. The filtrate was combined with the washings to obtain 3 liters of a solution containing 4762 γ/ml of cephalosporin C. 200 Milliliters of this solution was adjusted to pH 7.0 by addition of sodium hydroxide, incorporated with 350 mg. of cobalt sulfate and 194 mg. of piperazine and then heated to 37° C. Into this liquid, 3.4 g. of phenylglyoxal was dropped over a period of 1 hour with stirring. In this case, sodium hydroxidesulfuric acid was added so that the pH of the reaction liquid became 5.0. The liquid was further stirred at 37° C. for 30 minutes and then adjusted to pH 3.0 by addition of sulfuric acid. Into this liquid, 43.9 ml. of a saturated aqueous sodium perborate solution was dropped. After stirring for additional 10 minutes, the liquid was adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 70.1%.

This reaction liquid was treated in the same manner as in Example 2 to obtain 790 mg. of yellow crystals of 3-acetoxymethyl-7β-(4-carboxybutanamido)-3-cephem-4-carboxylic acid. Purity 72.2.

EXAMPLE 6

1.25 Grams of crystals of sodium salt of cephalosporin C having a purity of 74.2% and 791 mg. of nickel sulfate were dissolved in 100 ml. of water. To this liquid, 2.61 g. of glyoxylic acid and 204 mg. of imidazole were added with stirring at 5° C. The reaction liquid was adjusted to pH 5.0 by proper addition of an aqueous sodium hydroxide solution. After stirring the liquid for 2 hours, 53.0 ml. of a saturated aqueous potassium perborate solution was dropped into the liquid. The liquid was further stirred for 30 minutes and then adjusted to pH 1.5 by addition of hydrochloric acid to terminate the reaction. At this stage, the reaction liquid was analyzed to find that the crude yield of 3-acetoxymethyl-7β-(4-carboxybutanamido)-3-cephem-4-carboxylic acid was 81.4%.

This reaction liquid was treated in the same manner as in Example 2 to obtain 822 mg of pale yellow crystals of 3-acetoxymethyl-7β-(4-carboxybutanamido)-3-cephem-4-carboxylic acid. Purity 80.3%.

Entirely the same reaction as above was effected except that the nickel sulfate was replaced by the following metal salts.

| Metal salt | | Crude yield |
| --- | --- | --- |
| Kind | Amount (mg) | (mg) |
| $FeCl_3 \cdot 2H_2O$ | 436 | 838 |
| $AlCl_3 \cdot 6H_2O$ | 725 | 838 |
| $CaCl_2 \cdot 2H_2O$ | 442 | 811 |
| $FeSO_4 \cdot 7H_2O$ | 836 | 834 |
| $MnSO_4 \cdot H_2O$ | 509 | 831 |

EXAMPLE 7

2.3 Grams of crystals of sodium salt of cephalosporin C having a purity of 74.2% were dissolved in 300 ml. of a 2M phosphate buffer (pH 4.6). Into this liquid, 300 ml. of a 2M phosphate buffer (pH 4.6) containing 4.7 g. of sodium glyoxylate was gradually dropped over a period of 30 minutes with stirring at 5° C. This liquid was stirred and reacted for 2 hours, continuously incorporated with 33 ml. of a 15% aqueous hydrogen peroxide solution, further stirred for 15 minutes and then lowered in pH to 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 76.4%.

This reaction liquid was treated in the same manner as in Example 2 to obtain 1.65 g. of pale yellow crystals of 3-acetoxymethyl-7β-(4-carboxybutanamido)-3-cephem-4-carboxylic acid. Purity 68.7%.

EXAMPLE 8

375 Milligrams of crystals of sodium salt of cephalosporin C having a purity of 74.2% and 237 mg. of nickel sulfate were dissolved in 45 ml. of water. To this liquid, 620 mg. of pyruvic acid and 61.2 mg. of imidazole were added with stirring at room temperature. The reaction liquid was adjusted to pH 5.0 by proper addition of an aqueous sodium hydroxide solution. After stirring the liquid for 2 hours, 15.9 ml. of a saturated aqueous potassium perborate solution was dropped into the liquid. The liquid was further stirred for 30 minutes and then adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 77.6%.

This reaction liquid was treated in the same manner as in Example 2 to obtain 238 mg. of pale yellow crystals of 3-acetoxymethyl-7β-(4-carboxybutanamido)-3-cephem-4-carboxylic acid. Purity 79.6%.

EXAMPLE 9

Entirely the same reaction as in Example 2 was effected, except that 3 g. of crystals of sodium salt of deacetyl cephalosporin C having a purity of 56.3% were used in place of the crystals of sodium salt of cephalosporin C. In the course of the reaction, the crude yield of 3-hydroxymethyl-7β-(4-carboxybutanamido)-3-cephem-4-carboxylic acid in the reaction liquid was 90%. As the result of the reaction, 1.2 g. of pale yellow crystals of 3-hydroxymethyl-7β-(4-carboxybutanamido)-3-cephem-4-carboxylic acid were obtained. Purity 92.5%.

EXAMPLE 10

Entirely the same reaction as in Example 2 was effected, except that 5 g. of crystals of sodium salt of deacetoxy cephalosporin C having a purity of 83% were used in place of the crystals of sodium salt of cephalosporin C. In the course of the reaction, the crude yield of 3-methyl-7β-(4-carboxybutanamido)-3-cephem-4-carboxylic acid in the reaction liquid was 95.2%. As the result of the reaction, 3.0 g. of pale yellow crystals of 3-methyl-7β-(4-carboxybutanamido)-3-cephem-4-carboxylic acid were obtained. Purity 96.7%.

EXAMPLE 11

Entirely the same reaction as in Example 2 was effected, except that 3 g. of crystals of N-[7-D-(5-aminoadipinamido)-3-cephem-3-ylmethyl]-pyridium-4-carboxylic acid having a purity of 83.9% were used in place of the crystals of sodium salt of cephalosporin C. In the course of the reaction, the crude yield of N-[7-(4-carboxybutanamido)-3-cephem-3-ylmethyl]pyridinium-4-carboxylic acid was 82.0%. As the result of the reaction, 2.1 g of pale yellow crystals of N-[7-(4-carboxybutanamido)-3-cephem-3-ylmethyl]-pyridinium-4-carboxylic acid were obtained. Purity 86.0%.

EXAMPLE 12

Entirely the same reaction as in Example 7 was effected, except that 4.6 g. of glyoxylic acid amide was used in place of the sodium glyoxylate. In the course of the reaction, the crude yield of 3-acetoxymethyl-7β-(4-carboxybutanamido-3-cephem-4-carboxylic acid in the reaction liquid was 75.9%. As the result of the reaction, 1.65 g. of pale yellow crystals of 3-acetoxymethyl-7β-(4-carboxybutanamido)-3-cephem-4-carboxylic acid were obtained. Purity 67.9%.

EXAMPLE 13

1.3 Grams of crystals of sodium salt of cephalosporin C having a purity of 74.2% were dissolved in 250 ml. of water. This liquid was incorporated with 441 mg. of copper acetate, and the pH of the liquid was maintained at 5.0. To this liquid, 506 mg. of glyoxylic acid was added with stirring at room temperature. After stirring for 2 hours, the liquid was adjusted to pH 3.0 by addition of 1N sulfuric acid and then incorporated with 1.9 ml. of a 15% aqueous hydrogen peroxide solution. The liquid was further stirred for 10 minutes and then adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 77.3%.

This reaction liquid was treated in the same manner as in Example 2 to obtain 892 mg. of pale yellow crystals of 3-acetoxymethyl-7β-(4-carboxybutanamido)-3-cephem-4-carboxylic acid. Purity 68.8%.

EXAMPLE 14

1.9 Grams of crystals of sodium salt of cephalosporin C having a purity of 74.2% were dissolved in 350 ml. of water. This liquid was incorporated with 2 ml. of pyridine, and the pH of the liquid was maintained at 4.6. To this liquid, 736 mg. of glyoxylic acid was added with stirring at room temperature. After stirring for 2 hours, the liquid was adjusted to pH 3.0 by addition of 1N sulfuric acid and then incorporated with 2.5 ml. of a 25% aqueous hydrogen peroxide solution. The liquid was further stirred for 10 minutes and then adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 77.1%.

This reaction liquid was treated in the same manner as in Example 2 to obtain 1.3 g. of pale yellow crystals of 3-acetoxymethyl-7β-(4-carboxybutanamido)-3-cephem-4-carboxylic acid. Purity 68.3%.

EXAMPLE 15

A fermentation liquor of *Cephalosporium acremonium* was freed from the cells by filtration, subjected to acid treatment (pH 2.8) to decompose penicillin N contained therein and then again filtered, and the residue was washed. The filtrate was combined with the washings to obtain 3 liters of a solution containing 4762 γ/ml of cephalosporin C. 100 Milliliters of this solution was adjusted to pH 7.0 by addition of sodium hydroxide, incorporated with 175 mg. of cobalt sulfate and 97 mg. of piperazine, and then heated to 37° C. Into this liquid, 1.9 g. of α-ketophenylacetic acid was dropped over a period of 1 hour with stirring while maintaining the pH at 5.0. The liquid was further stirred at 37° C. for 30 minutes and then adjusted to pH 3.0. Into this liquid, 22 ml. of a saturated aqueous sodium perborate solution was dropped. After stirring for additional 10 minutes, the liquid was adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 60.3%.

This reaction liquid was treated in the same manner as in Example 2 to obtain 355 mg. of yellow crystals of 3-acetoxymethyl-7β-(4-carboxybutanamido)-3-cephem-4-carboxylic acid. Purity 68.7%.

EXAMPLE 16

6.7 Grams of crystals of sodium salt of cephalosporin C having a purity of 51.3% and 1.6 g. of copper acetate were dissolved in 600 ml. of a 2M phosphate buffer (pH 4.6). Into this liquid, 600 ml. of a 2M phosphate buffer (pH 4.6) containing 8.4 g. of sodium α-keto-n-butanoate was gradually dropped over a period of 30 minutes with stirring at 5° C. This liquid was stirred and reacted for 30 minutes, gradually incorporated with 30 ml. of a 35% aqueous hydrogen peroxide solution, further stirred for 10 minutes and then lowered in pH to 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 63.2%.

This reaction liquid was treated in the same manner as in Example 2 to obtain 1.92 g. of pale yellow crystals of 3-acetoxymethyl-7β-(4-carboxybutanamido)-3-cephem-4-carboxylic acid. Purity 66.3%.

EXAMPLE 17

4 Grams of crystals of sodium salt of cephalosporin C having a purity of 74.2% and 3.3 g. of copper acetate were dissolved in 120 ml. of water. At this stage, the pH of the reaction liquid was 3.9. Into this reaction liquid, 120 ml. of an aqueous solution containing 6.24 g. of glyoxylic acid and 5.5 ml. of pyridine was dropped over a period of 1 hour with stirring at room temperature. The pH of the reaction liquid at the time of completion of the reaction was 4.6. Thereafter, the reaction liquid was adjusted to pH 3.0 by addition of 1N sulfuric acid, and 60 cc. of a 15% aqueous hydrogen peroxide solution was dropped into the liquid over a period of 1 hour. This liquid was stirred for 10 minutes, incorporated with 21.9 g. of sodium thiosulfate, further stirred for 10 minutes and then adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 92%. No 3-acetoxymethyl-7β-(5-carboxy-5-oxopentanamido)-3-cephem-4-carboxylic acid was detected.

This reaction liquid was extracted 3 times with 500 ml. of ethyl acetate, and the extracts were collected. The collected ethyl acetate extract was concentrated under reduced pressure at below 40° C. to a volume of about 200 ml. and then dried overnight by use of anhydrous sodium sulfate. This liquid was filtered, and then the residue was washed with a small amount of ethyl acetate. The filtrate was combined with the washings, and the resulting liquid was concentrated under reduced pressure at below 40° C. to a volume of 10 ml. and then dropped into 200 ml. of petroleum ether with vigorous stirring. This liquid was subjected to centrifugation, and the supernatant was removed by decantation. Thereafter, the precipitate was suspended in petroleum ether, and the resulting suspension was again subjected to centrifugation. After removing the supernatant by decantation, the precipitate was quickly dried over alumina in vacuum to obtain 2.43 g. of pale yellow crystals of 3-acetoxymethyl-7β-(4-carboxybutanamido)-3-cephem-4-carboxylic acid. Purity 98.9%.

EXAMPLE 18

1.5 Grams of crystals of sodium salt of cephalosporin C having a purity of 74.2% and 406 mg. of copper sulfate were dissolved in 100 ml. of water. At this stage, the pH of the reaction liquid was 3.9. To this liquid, each 20 ml. of 100 ml. of an aqueous solution containing 2.3 g. of glyoxylic acid and 1.5 ml. of triethylamine was added every 30 minutes with stirring at room temperature. When 10 minutes had elapsed after each addition, each 3 ml. of a 20% aqueous hydrogen peroxide solution was added and the liquid was reacted with stirring for 30 minutes. The pH of the reaction liquid at the time of completion of the reaction was 3.5. After stirring for additional 30 minutes, the reaction liquid was incorporated with 6.29 g. of sodium thiosulfate, further stirred for 10 minutes and then adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 87.8%.

This reaction liquid was treated in the same manner as in Example 17 to obtain 0.88 g. of pale yellow crystals of 3-acetoxymethyl-7β-(4-carboxybutanamido)-3-cephem-4-carboxylic acid. Purity 97.1%.

EXAMPLE 19

4 Grams of crystals of sodium salt of cephalosporin C having a purity of 74.2% and 3.3 g. of copper acetate were dissolved in 120 ml. of water. At this stage, the pH of the reaction liquid was 3.9. Into this reaction liquid, 120 ml. of an aqueous solution containing 6.24 g. of glyoxylic acid and 5.5 ml. of pyridine was dropped over a period of 1 hour with stirring at room temperature. The pH of the reaction liquid at the time of completion of the reaction was 4.6. Thereafter, the reaction liquid was adjusted to pH 3.0 by addition of 1N sulfuric acid, and 60 cc. of a 15% aqueous hydrogen peroxide solution was dropped into the liquid over a period of 1 hour. The reaction liquid was stirred for 10 minutes, incorporated with 21.9 g. of sodium thiosulfate pentahydrate, further stirred for 10 minutes and then adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 92%. No 3-acetoxymethyl-7β-(5-carboxy-5-oxopentanamido)-3-cephem-4-carboxylic acid was detected.

This reaction liquid was extracted 3 times with ethyl acetate, and the extracts were collected. The collected ethyl acetate extract was concentrated under reduced pressure at below 40° C to a volume of about 200 ml. and then dried overnight by use of anhydrous sodium sulfate. This liquid was filtered, and the residue was washed with a small amount of ethyl acetate. The filtrate was combined with the washings, and the resulting liquid was concentrated under reduced pressure at below 40° C. to a volume of 10 ml. and then dropped into 200 ml. of petroleum ether with vigorous stirring. This liquid was subjected to centrifugation, and the supernatant was removed by decantation. Thereafter, the precipitate was suspended in petroleum ether, and the resulting suspension was again subjected to centrifugation. After removing the supernatant by decantation, the precipitate was quickly dried over alumina in vacuum to obtain 2.43 g. of pale yellow crystals of 3-acetoxymethyl-7β-(4-carboxybutanamido)-3-cephem-4-carboxylic acid. Purity 98.9%.

EXAMPLE 20

1.5 Grams of crystals of sodium salt of cephalosporin C having a purity of 74.2% and 406 mg. of copper sulfate were dissolved in 100 ml. of water. At this stage, the pH of the reaction liquid was 3.9. To this liquid, each 20 ml. of 100 ml. of an aqueous solution containing 2.3 g. of glyoxylic acid and 1.5 ml. of triethylamine was added every 30 minutes with stirring at room temperature. When 10 minutes had elapsed after each addition, each 3 ml. of a 20% aqueous hydrogen peroxide solution was added, and the liquid was reacted with stirring for 30 minutes. The pH of the reaction liquid at the time of completion of the reaction was 3.5. After stirring for additional 30 minutes, the reaction liquid was incorporated with 6.29 g. of sodium thiosulfate pentahydrate, further stirred for 10 minutes and then adjusted to pH 1.5 by addition of sulfuric acid to terminate the reaction. At this stage, the reaction liquid was analyzed to find that the crude yield of 3-acetoxymethyl-7β-(4-carboxybutanamido)-3-cephem-4-carboxylic acid was 87.8%.

This reaction liquid was treated in the same manner as in Example 19 to obtain 0.88 g. of pale yellow crystals of 3-acetoxymethyl-7β-(4-carboxybutanamido)-3-cephem-4-carboxylic acid. Purity 97.1%.

What is claimed is:

1. A process for preparing α-ketoadipoyl 7-aminocephalosporanic acid or its derivative represented by the formula (IV),

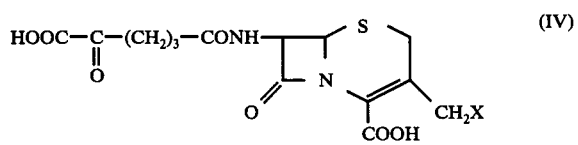

wherein X is hydrogen, hydroxyl, acetoxy or pyridyl and 7-aminocephalosporanic acid derivatives represented by the formula (III),

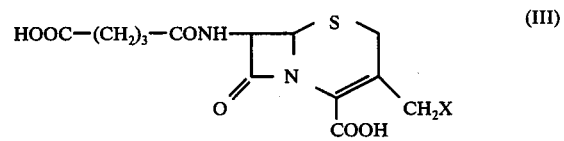

wherein X is as defined above, which comprises reacting cephalosporin C or its derivative represented by the formula (I),

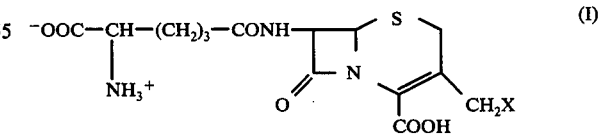

wherein X is as defined above, or a sodium salt thereof with an α-keto derivative selected from the group consisting of glyoxylic acid, pyruvic acid, phenylglyoxal, glyoxylic acid amide, α-keto-phenylacetic acid, sodium α-keto-n-butanoate, α-keto-n-butanoic acid and sodium glyoxylate.

2. A process for preparing 7-aminocephalosporanic acid derivatives represented by the formula (III),

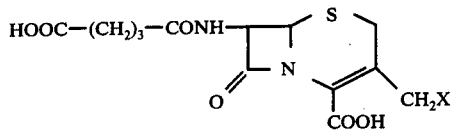

wherein X is hydrogen, hydroxyl, acetoxy or pyridyl, which comprises reacting cephalosporin C or its derivative represented by the formula (I),

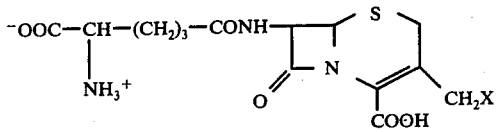

wherein X is as defined above, or a sodium salt thereof with an α-keto derivative selected from the group consisting of glyoxylic acid, pyruvic acid, phenylglyoxal, glyoxylic acid amide, α-keto-phenylacetic acid, sodium α-keto-n-butanoate, α-keto-n-butanoic acid and sodium glyoxylate in the presence of hydrogen peroxide.

3. A process according to claim 2, wherein the cephalosporin C or its derivative of the formula (I) or the sodium salt thereof is reacted with the α-keto derivative and the reaction mixture is then treated with hydrogen peroxide.

4. A process according to claim 3, wherein the reaction mixture is further treated with thiosulfuric acid or a sodium salt thereof to decompose the unreacted hydrogen peroxide.

5. A process according to claim 1, wherein said α-keto derivative is selected from glyoxylic acid, phenylglyoxal and glyoxylic acid amide.

6. A process according to claim 1, wherein said α-keto derivative is selected from pyruvic acid, α-ketophenylacetic acid and α-keto-n-butanoic acid.

7. A process according to claim 1, wherein the α-keto derivative is used in an amount of 1 to 50 times the molar amount of the cephalosporin C or its derivative of the formula (I) or the sodium salt thereof.

8. A process according to claim 7, wherein the reaction of the cephalosporin C or its derivative of the formula (I) or the sodium salt thereof with the α-keto derivative is carried out at a pH of 3.0 to 8.0.

9. A process according to claim 8, wherein the reaction of the cephalosporin C or its derivative of the formula (I) or the sodium salt thereof with the α-keto derivative is carried out in the presence of a bivalent or trivalent metal ion selected from the group consisting of copper, manganese, calcium, aluminum, iron, nickel, cobalt and zinc ions.

10. A process according to claim 9, wherein said metal is selected from copper, manganese, calcium, aluminum, iron, nickel and cobalt.

11. A process according to claim 10, wherein the amount of the metal ion used is 1/10 to 20 times the molar amount of the cephalosporin C or its derivative of the formula (I) or the sodium salt thereof.

12. A process according to claim 8, wherein the reaction of the cephalosporin C or its derivative of the formula (I) or the sodium salt thereof with the α-keto derivative is carried out in the presence of an organic base selected from the group consisting of tertiary cyclic amines, secondary cyclic amines and $C_1$–$C_2$ alkylamines.

13. A process according to claim 12, wherein said organic base is selected from pyridine, picolines, imidazole, piperazine and $C_1$–$C_2$ alkylamines.

14. A process according to claim 12, wherein the amount of the organic base used is 1 to 30 times the molar amount of the cephalosporin C or its derivative of the formula (I) or the sodium salt thereof.

15. A process according to claim 8, wherein the reaction of the cephalosporin C or its derivative of the formula (I) or the sodium salt thereof with the α-keto derivative is carried out at a temperature of 0° to 50° C.

16. A process according to claim 15, wherein the reaction of the cephalosporin C or its derivative of the formula (I) or the sodium salt thereof with the α-keto derivative is carried out for 5 minutes to 24 hours.

17. A process according to claim 2, wherein the amount of hydrogen peroxide used is 1 to 30 times the molar amount of the cephalosporin C or its derivative of the formula (I) or the sodium salt thereof.

18. A process according to claim 17, wherein the reaction of the cephalosporin C or its derivative of the formula (I) or the sodium salt thereof with the α-keto derivative is carried out at a pH of 2.0 to 6.0.

19. A process according to claim 18, wherein the reaction of the cephalosporin C or its derivative of the formula (I) or the sodium salt thereof with the α-keto derivative is carried out at a temperature of 0° to 50° C.

20. A process according to claim 19, wherein the reaction of the cephalosporin C or its derivative of the formula (I) or the sodium salt thereof with the α-keto derivative is carried out for 10 minutes to 5 hours.

* * * * *

UNITED STATES PATENT AND TRADEMARK OFFICE
CERTIFICATE OF CORRECTION

PATENT NO. : 4,079,180
DATED : March 14, 1978
INVENTOR(S) : SUZUKI ET AL

It is certified that error appears in the above-identified patent and that said Letters Patent are hereby corrected as shown below:

Claim 1: In Formulas I, III and IV, the portion of the formula written as:

" 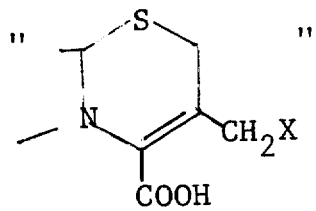 "   should read   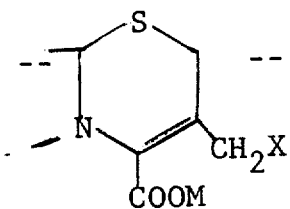

Please cancel the line following Formula IV (i.e., Col. 14, line 39) and insert therefor: --wherein X is hydrogen, hydroxyl or acetoxy and M is hydrogen and wherein M is a negative charge when X is pyridinio--.

UNITED STATES PATENT AND TRADEMARK OFFICE
CERTIFICATE OF CORRECTION

PATENT NO. : 4,079,180
DATED : March 14, 1978
INVENTOR(S) : SUZUKI ET AL

It is certified that error appears in the above-identified patent and that said Letters Patent are hereby corrected as shown below:

Claim 2: In Formulas I and III, the portion of said formulas written as:

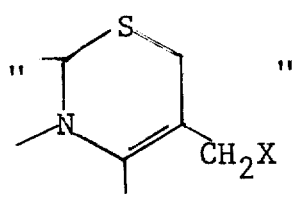   should read   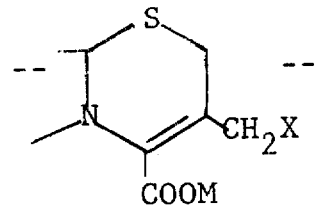

Please cancel the line following Formula III (i.e., Col. 15, line 8) and replace the cancelled line with --wherein X is hydrogen, hydroxyl or acetoxy and M is hydrogen and wherein M is a negative charge when X is pyridinio,--

Signed and Sealed this

Thirty-first Day of March 1981

[SEAL]

Attest:

RENE D. TEGTMEYER

Attesting Officer    Acting Commissioner of Patents and Trademarks